United States Patent [19]

Villette

[11] Patent Number: 4,944,678

[45] Date of Patent: Jul. 31, 1990

[54] PROCESS AND APPARATUS FOR DEVITALIZATION OF A TOOTH

[75] Inventor: Alain Villette, St. Pierre des Echaubrognes, France

[73] Assignee: Bristol-Myers-Squibb Company, New York, N.Y.

[21] Appl. No.: 153,122

[22] Filed: Feb. 8, 1988

[51] Int. Cl.⁵ ............................................... A61C 5/02
[52] U.S. Cl. ...................................... 433/224; 433/81
[58] Field of Search ................................. 433/224, 81

[56] References Cited

U.S. PATENT DOCUMENTS 3,079,690  3/1963  Lodige .................................. 433/81
4,006,736  2/1977  Kranys et al. ...................... 128/655
4,357,136  11/1982 Herskovitz et al. ................ 433/224
4,684,344  8/1987  Brockway et al. ................... 433/81

FOREIGN PATENT DOCUMENTS 483465  10/1929  Fed. Rep. of Germany ........ 433/81

Primary Examiner—John J. Wilson
Attorney, Agent, or Firm—Thomas A. O'Rourke

[57] ABSTRACT

A process for devitalization for a tooth in which, after drilling of a small hole through the crown into the pulp cavity, an inert paste is injected under pressure into the pulp cavity and into the root-canal causing a desiccation of the pulp tissues and the devitalization of the tooth.

18 Claims, 2 Drawing Sheets

PROCESS AND APPARATUS FOR DEVITALIZATION OF A TOOTH

BACKGROUND OF THE INVENTION

The present invention relates to improvements in endodontics or root canal therapy. More specifically, it relates to processes of devitalization of teeth as well as the means of practicing the process.

The "devitalization" of a tooth by removal of the pulp and replacement with an inert cement-like substance, is an extremely common operation in dental surgery. Despite advances in dental therapeutics and anesthetics, root canal surgery can be a painful experience for the patient. The term "root canal surgery" or "devitalization" means extraction of the pulp or a pulpectomy. Dental pulp is the richly vascularized innervated connective tissue contained in the pulp cavity of the tooth. It constitutes the formative, nutritive and sensory organ of the dentin. Pulp contains nerves and many vessels such as arteries, veins and lymph vessels and is composed chiefly of cells and connective tissue. Pulp is appreciably softer than the outer enamel and the dentin and consists primarily of a layer of cells (odontoblasts) which secrete the secondary dentin onto the interior wall of the tooth. The pulp terminates at the bottom of the tooth in a funnel or apex shape.

Under normal circumstances, the pulp is protected from infection. However, infections can arise when decay or caries spreads through the enamel and dentin or when fillings crack and expose the soft tissue. Infections may also arise when the tooth is dislodged or suffers trauma. If the infection remains untreated there is a serious risk of the infection spreading through the tooth's roots into the supporting bone structure. The usual procedure in endodontics is to remove the infected pulp and/or the damaged nerve, followed by sterilization of the tooth's roots. Finally, the area is sealed with an inert paste to protect it from future infections.

One method of devitalization consists of the use of an arsenic compound, $As_2O_3$, which acts by vasodilation. The dilation of the arteries causes a constriction of the veins so that the blood can no longer circulate. Once circulation ceases, necrosis of the tissue commences.

As soon as necrosis is achieved, a wide opening in the upper surface of the tooth is formed. Instruments such as a broach, a barbed broach and files are used in root canal surgery. Once the opening in the tooth is of sufficient size, an inert paste is introduced by means of a lentula (small endless screw) which is designed to force the paste into the cavity. One of the drawbacks in the use of the barbed broach is that it extirpates the pulp, causing a tissue laceration.

A second commonly employed method of root canal surgery is almost identical to the first, except that the first stage of the process consists of administering a local anesthetic such as lidocaine, instead of the use of the arsenic compound. The anesthesia usually makes it possible to conduct the necessary dental operations without the patient experiencing intolerable pain. However, because of the mechanical aggravation of the dental tissue caused by the surgery, patients frequently suffer continued pain once the initial anesthesia abates. Thus, the surgeon is often obliged to prescribe further pain relievers to reduce the patient's discomfort.

The canals present in the tooth are extremely contorted in shape (elbows, reverse elbows, bayonets, etc.), so that it is not always possible to completely fill the canals with the inert paste. Because of the contorted shape of many canals, broaches are employed to ream the canal and straighten it. Frequently, files also have to be used to straighten the canal. Once the canal has been straightened, the soft tissues can be replaced with the inert hard paste. Prior to introduction of the paste into the cavity, it is necessary to completely dry the cavities to be filled. Paper cones are usually employed for this purpose.

The paste used in root canal surgery is hydrophobic, and comprises a base consisting of a radiopaque powder and a biocompatible oil. Accordingly, in order to obtain a good tight filling with the paste, it is imperative for the cavity to be perfectly dry. The paper cones dry the canals by a kind of pumping action. The inert paste is then placed into the pulp chamber and is forced into the channels by means of lentulas (endless screws) which force the paste into the cavity. To avoid air bubbles, cones of gutta-percha, resin, silver, etc., are placed inside the canal.

In current dental practices in the United States, the lentula is not used. Instead the canals are enlarged. Gutta-percha is then placed in the canals and is heated, which causes the gutta-percha to melt and condense along the canal walls. Unfortunately, this is time intensive and takes from one hour to an hour and a half for each canal. An electrically powered and heated endodontic syringe for this purpose is disclosed, for example, in U.S. Pat. No. 4,684,344. In this patent there is disclosed a syringe which includes a drive motor and mechanism for translation of a plunger, a gutta-percha cartridge and heating element surrounding the cartridge.

SUMMARY OF THE INVENTION

A completely novel procedure has now been discovered to effect replacement of the tooth pulp with an inert paste. The procedure greatly facilitates the operations required by the dental surgeon while at the same time limiting patient trauma. In accordance with the process of the invention the dental paste used to replace the pulp in the pulp cavity is forced into the cavity through an opening in the covering in the tooth. The paste is injected under sufficient pressure so that the water and other cellular fluids in the dental pulp are forced out of the cavity and the connective tissue, cell membrane and other solid material are compressed against the periphery of the pulp cavity which, since it is dessicated and protected by the dental paste, becomes an inert material in which no bacterial growth takes place.

Apparatus is provided for achieving the process of the invention.

DRAWING

FIG. 1 is a cross-sectional enlarged view showing a tooth in vertical section, during the process according to the invention.

DETAILED DESCRIPTION

Figure 1:
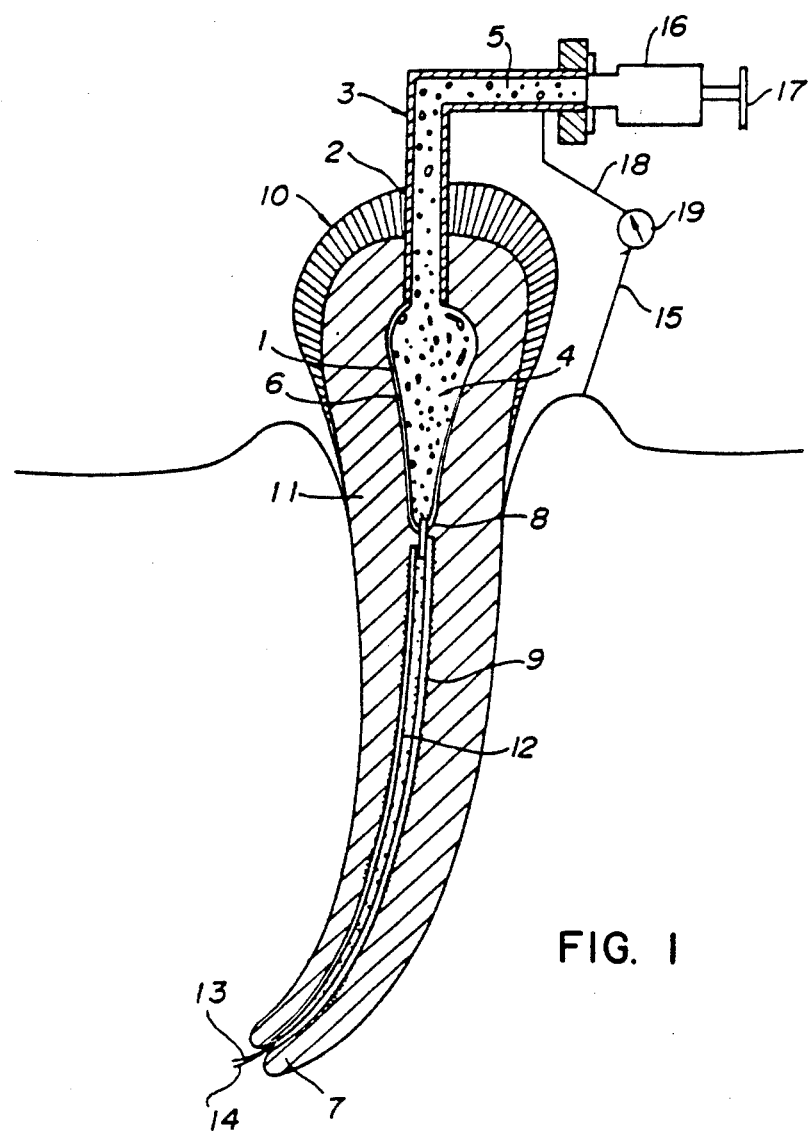

The following particular dental procedure is described as an example of the technique embodying the present invention which is referred hereunder as OBTURATION BY COMPRESSION or "OPC".

Referring to the drawing, the enamel 10 surrounds the dentin 11 of the upper or crown section of the tooth.

An orifice 2 slightly cone-shaped in configuration is forced through the crown and into the pulp cavity 4, suitably by drilling. Into the orifice 2 is screwed a cannula 3 the proximate end of which terminates at the pulp cavity 4, the distal end being in cooperative engagement with an injector 16 or other means to permit the injection of an inert dental paste 5 into the pulp cavity.

The patient may be under general anesthesia, but local anesthesia is usually adequate. The injection of the inert paste causes the pulp 6 to be forced against the dentin wall 1. The blood circulation continues in the root-canal 9 through arteries and veins which, for convenience, are shown as artery 13 and vein 14. In the root-canal 9, arterioveinous shunts 12 provide a blood irrigation, even after the pulp in the pulp chamber has been desiccated.

In the process of the present invention, a local anesthesia is initially administered to the patient.

Typically, the major or the external average diameter of the cone-shaped orifice 2 is about 1.25 to 1.75 millimeter. The minor or internal diameter is about 0.8 to 1 mm. A cannula is mounted within the orifice 2, preferably by screwing. It is important that the cannula be securely fitted within the orifice so that the cannula will not be driven out under the effect of the pressure of the inert paste.

Preferably, the cannula is filled with the inert paste before it is mounted in the orifice to avoid introduction of air bubbles into the pulp chamber 4. Then, a syringe, or other injector means 16, containing additional inert paste is mounted on the distal end of the cannula.

The inert paste or filler must be biologically inert. Many suitable materials will be known to those skilled in the art. One such material comprises calcium phosphate salts such as "triosite" which is principally calcium triphosphate mixed with a suitable amount biocompatible oil such as glycerin to produce a paste with a suitable viscosity. The paste should be sufficiently viscous so that it does not flow uncontrollably through the aperture of the cannula. On the other hand, if the paste is too viscous, it will not pass into the small canals of the tooth.

It has been observed that with pastes of the desired viscosity such that they will not pass through the cannula, but will fill the small canals of the tooth, a pressure of about 40 to about 60 kg./cm$^2$ is normally sufficient although higher pressures are permissible. Typically, the pressure employed is about 50 kg./cm$^2$. Any of a variety of pressure applying means can be employed. A simple plunger 17 in a tube may serve as a convenient injector means 16.

The paste enters the tooth and it has been observed that the paste forces all of the pulp against the internal wall of the tooth. The pulp tissue is compressed against the dentin wall 1. The paste is injected at the upper part of the pulp cavity and may descend to the apical constriction 8. It is usually preferred that the paste go no further than the apical constriction 8 because it permits the blood to continue to circulate through the arterioveinous shunts 12 to maintain the strength of the tooth. Depending on the condition of the tooth, it may also not be necessary that the paste descend to the apical constriction 8 thereby keeping alive a maximum amount of pulp.

As described above, the pressure applied by the injector is one which is appropriate to the selected viscosity of the paste. This viscosity is chosen so that at the selected pressure the paste stops at the apical constriction 8 in the tooth. The paste is injected from top to bottom in the pulp cavity, so that there can be no bubbles. The cavity itself determines the path of the paste by serving as a mold and the paste travels under the pressure wherever there is soft tissue.

Injection into the pulp cavity of a high viscosity paste creates a compression that forces the pulp tissue against the rigid dentin 1 wall and eliminates tissue fluids. The tissue fluids are absorbed by the blood circulation through the apex 7. The remaining tissue is reduced to a thin membrane in which no water remains and thus no bacterial growth can occur.

If necessary, the material injected may be pushed from the pulp chamber into the root-canals up to the apex 7, if desired, and crushing soft tissues in the root-canals as well as in the pulp chamber.

Figure 2:
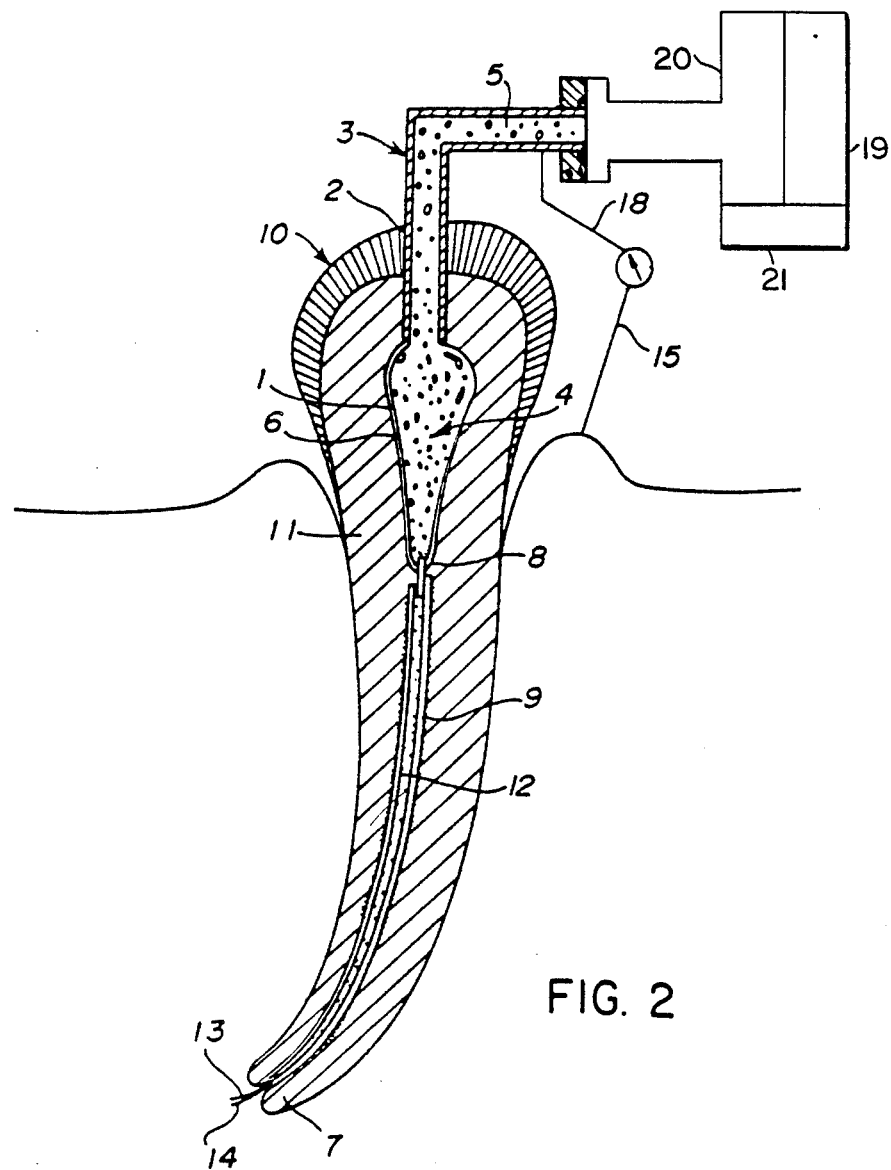

As indicated above, appreciable pressure is required to inject a highly viscous material into the fine canals of the tooth. Accordingly, the rate of injection must be slow in order to avoid any tooth fracture. All these requirements (high pressure, slow injection and safety) are conveniently achieved by an injector means including a plunger, having a short axial movement of from about 2 to 5 mm. and a barrel having an internal diameter of about 2 to 3.5 mm. to reduce the needed force. As shown in FIG. 2, in one suitable arrangement, the plunger is driven by a motoreductor 19 cooperating with an electrically controlled endless screw 20. Alternatively, it is possible to use a manually-controlled injector. To avoid fracturing of the tooth resistance in the manually-controlled injector has a pressure limit means 21 which may be calibrated so that the pressure is broken (halted) if excess pressure over a set pressure is reached during any stage of the injection. Thus, fracturing of the tooth will be avoided. The range of injection pressure is generally from 40 kg./cm$^2$ to 133 kg./cm$^2$.

It is desirable to monitor the level of the paste inside the tooth during the injection process. One suitable procedure is to follow the level by radiography. Alternatively, the paste may be monitored by the inclusion of microfined gold powder which is opaque to x-rays in the paste. Another procedure is to utilize an electroconductive paste and to follow the level by observing changes in electric resistance between two electrodes 15 and 18. One of the electrodes 15 may be inserted in the tooth while the other 18 is on the injector or cannula. This procedure is based on the fact that a vital pulp has a constant electric resistance. The variation of the resistance can be extrapolated to the level of filling in the cavity. Measuring the variations of resistance of the circuit between the paste and the pulp by a measuring means 19 permits the practitioner to know the level of the paste in the canal.

Thus, the OPC technique of the present invention involves no extraction of pulp tissue and the repair process is considerably facilitated. Compared to conventional techniques, far less equipment is required in practicing the present invention than in the prior art. Using the injector for filling the cavity will eliminate expensive and fragile tools like broaches, reamers, rotary bars, spreaders, pluggers, paste fillers, compactors, root-canals, irrigation devices and so on.

It has been observed that the technique of this invention did not result in any type of inflammatory pulp damage and it eliminated all risk of microbial infection. This method is applicable to the treatment of deciduous teeth as well as permanent teeth.

The pulp tissue left in contact with the filling material presents a normal parenchyma and the odontoblasts, normally distributed, do not show any alteration, the thickness and structure of the predentin being also normal. Only the predentin-pulpal border shows a slightly scalloped aspect which indicates a dystophic process of only little importance.

A particular advantage of this invention is the speed with which it can be accomplished. Previous procedures required about one to one and a half hour per canal, thus about three to four hours were necessary for devitalization of one tooth. According to the present invention, treatment may be accomplished in as little as about one quarter of an hour.

I claim:

1. An apparatus for devitalization of a tooth by obduration comprising a cannula which is adapted to be inserted into an orifice in the crown section of a tooth such that said cannula is removably retained within said orifice and enters and terminates at the pulp cavity of said tooth and an injector means, said injector means being adapted to inject an inert paste into said cavity and a means to terminate the pressure on the inert paste whenever a predetermined pressure is reached during injection and a means to monitor the level of paste inside the tooth during the injection process, said injector means being adapted to inject an inert paste into a tooth such that said paste compresses the pulp tissue of said tooth against the dentin wall and eliminates tissue fluids in the pulp.

2. The apparatus of claim 1 wherein said injector has a plunger having a short axial movement of about 2.5 mm. to 5 mm. and a barrel of about 2 to 3.5 mm. in diameter.

3. The apparatus of claim 2 wherein the plunger is driven by an electrically-controlled motoreductor co-operating with an endless screw.

4. The apparatus of claim 1 wherein said injector means is adapted to inject an inert paste into the pulp cavity at a pressure of about 40 to 60 kg./cm$^2$.

5. The apparatus of claim 4 wherein said injector means has a pressure limit means to break the pressure of the paste if it exceeds a selected pressure.

6. The apparatus of claim 4 wherein said injector means i adapted to inject an inert paste into the pulp cavity at a pressure of about 50 kg./cm$^2$.

7. A process of devitalization of a tooth by obturation which comprises injecting an inert dental paste through an orifice in the crown section of the tooth into the pulp cavity under sufficient pressure to effect dessication and compression of the pulp in the pulp cavity and replacement thereof with the paste.

8. A process according to claim 7 wherein the pressure is from about 40 to 60 kg./cm$^2$.

9. A process according to claim 7 wherein the level of the paste is monitored during the injection process.

10. A process of devitalization of a tooth which comprises forming a cone shaped orifice in the crown of the tooth into the pulp cavity, securing a cannula in said orifice, said cannula being operatively connected to an injector means and injecting an inert dental paste into the pulp cavity through the cannula utilizing pressure generated by the injector means, said pressure being sufficient to effect dessication and compression of the pulp in the pulp cavity and replacement thereof with the paste.

11. A process according to claim 10 wherein the pressure is from about 40 to 60 kg./cm$^2$.

12. A process according to claim 10 wherein the level of the paste is monitored during the injection process.

13. A process according to claim 10 or 8 wherein the level of the paste is measured by radiography.

14. A process according to claim 10 or 8 wherein the level of the paste is measured by x-rays.

15. A process according to claim 10 or 8 wherein the level of the paste is measured by electrical resistance.

16. An apparatus for devitalization of a tooth by obduration comprising a cannula which is adapted to be inserted into an orifice in the crown section of a tooth such that said cannula is removably retained within said orifice and enters and terminates at the pulp cavity of said tooth and an injector means said injector means being adapted to inject an inert paste into said cavity at a pressure of about 40 kg/cm$^2$ to 133 kg/cm$^2$ and a means to terminate the pressure on the inert paste whenever a predetermined pressure is reached during injection, said injector means being adapted to inject an inert paste into a tooth such that said paste compresses the pulp tissue of said tooth against the dentin wall and eliminates tissue fluids with the pulp.

17. An apparatus for devitalization of a tooth by obduration comprising a cannula which is adapted to be inserted into an orifice in the crown section of a tooth such that said cannula is removably retained within said orifice and enters and terminates at the pulp cavity of said tooth and an injector means, said injector means being adapted to inject an inert paste into said cavity at a pressure of about 40 kg/cm$^2$ to 133 kg/cm$^2$ and a means to terminate the pressure on the inert paste whenever a predetermined pressure is reached during injection and a means to monitor the level of paste inside the tooth during the injection process, said injector means being adapted to inject an inert paste into a tooth such that said paste compresses the pulp tissue of said tooth against the dentin wall and eliminates tissue fluids in the pulp.

18. An apparatus according to claim 17 wherein said means for monitoring the level of paste measures changes in electrical resistance between a first electrode inserted in the tooth and a second electrode on said injector or cannula.

* * * * *